(12) United States Patent
Lake et al.

(10) Patent No.: US 8,177,823 B2
(45) Date of Patent: May 15, 2012

(54) ORTHOPEDIC CLAMPING HOOK ASSEMBLY

(75) Inventors: Matthew Lake, Dedham, MA (US); Mark Hall, Bridgewater, MA (US); David Konieczynski, Needham, MA (US)

(73) Assignee: DePuy Spine Sarl, Le locle (CH)

( * ) Notice: Subject to any disclaimer, the term of this patent is extended or adjusted under 35 U.S.C. 154(b) by 1298 days.

(21) Appl. No.: 11/174,169

(22) Filed: Jun. 30, 2005

(65) Prior Publication Data
US 2007/0016189 A1  Jan. 18, 2007

(51) Int. Cl.
*A61B 17/84* (2006.01)
*A61B 17/70* (2006.01)

(52) U.S. Cl. ......... 606/330; 606/276; 606/277; 606/324

(58) Field of Classification Search .................. 606/276, 606/251–253, 330, 277, 324
See application file for complete search history.

(56) References Cited

U.S. PATENT DOCUMENTS

| | | | |
|---|---|---|---|
| D23,917 S * | 12/1894 | Lane et al. ..................... | D8/397 |
| 2,200,120 A | 5/1940 | Nauth | |
| D134,789 S * | 1/1943 | Gade .............................. | D8/397 |
| 2,466,023 A | 4/1949 | Griffin | |
| 3,835,849 A | 9/1974 | McGuire | |
| 4,299,212 A | 11/1981 | Goudfrooy | |
| 4,502,475 A | 3/1985 | Weigle et al. | |
| 4,686,972 A | 8/1987 | Kurland | |
| 4,815,453 A | 3/1989 | Cotrel | |
| 4,841,959 A | 6/1989 | Ransford | |
| 4,887,595 A | 12/1989 | Heinig et al. | |
| 5,024,213 A | 6/1991 | Asher et al. | |
| 5,127,912 A | 7/1992 | Ray et al. | |
| 5,129,900 A | 7/1992 | Asher et al. | |
| 5,176,680 A | 1/1993 | Vignaud et al. | |
| 5,180,381 A | 1/1993 | Aust et al. | |
| 5,190,543 A | 3/1993 | Schlapfer | |
| 5,217,461 A | 6/1993 | Asher et al. | |
| 5,257,993 A | 11/1993 | Asher et al. | |
| 5,261,912 A | 11/1993 | Frigg | |
| 5,303,694 A | 4/1994 | Mikhail | |
| 5,306,275 A | 4/1994 | Bryan | |
| 5,312,404 A | 5/1994 | Asher et al. | |

(Continued)

FOREIGN PATENT DOCUMENTS
FR  2642642 A1  8/1990
(Continued)

OTHER PUBLICATIONS

Faure, Alexis et al., "Inverted-hook occipital clamp system in occipitocervical fixation," *J. Neurosurg. (Spine 1)*, vol. 97:135-141 (2002).

(Continued)

*Primary Examiner* — Eduardo C Robert
*Assistant Examiner* — Julianna N Harvey
(74) *Attorney, Agent, or Firm* — Nelson Mullins Riley & Scarborough LLP (57) ABSTRACT

An occipital clamping hook assembly includes a hook for engaging a first side of an occipital bone and a compressor movable relative to the hook for applying a compressive force to the occipital bone from a second side of the occipital bone. The occipital clamping assembly further includes a rod-receiving portion coupled to the hook for coupling a rod to the occipital bone engaged by the hook.

14 Claims, 12 Drawing Sheets

U.S. PATENT DOCUMENTS

| | | | |
|---|---|---|---|
| 5,312,411 A | 5/1994 | Steele et al. | |
| 5,360,429 A | 11/1994 | Jeanson et al. | |
| 5,375,286 A | 12/1994 | Harrah | |
| 5,395,372 A | 3/1995 | Holt et al. | |
| 5,415,659 A | 5/1995 | Lee et al. | |
| 5,423,826 A | 6/1995 | Coates et al. | |
| 5,443,467 A | 8/1995 | Biedermann et al. | |
| 5,484,440 A | 1/1996 | Allard | |
| 5,490,822 A | 2/1996 | Biedermann | |
| 5,501,684 A | 3/1996 | Schlapfer et al. | |
| 5,507,745 A | 4/1996 | Logroscino et al. | |
| 5,520,689 A | 5/1996 | Schlapfer et al. | |
| 5,534,001 A | 7/1996 | Schlapfer et al. | |
| 5,542,946 A | 8/1996 | Logroscino et al. | |
| 5,545,164 A | 8/1996 | Howland | |
| 5,545,165 A | 8/1996 | Biedermann et al. | |
| 5,558,622 A | 9/1996 | Greenberg | |
| 5,575,792 A * | 11/1996 | Errico et al. | 606/276 |
| 5,584,832 A * | 12/1996 | Schlapfer | 606/276 |
| 5,591,167 A | 1/1997 | Laurain et al. | |
| 5,593,408 A | 1/1997 | Gayet et al. | |
| 5,601,552 A | 2/1997 | Cotrel | |
| 5,601,553 A | 2/1997 | Trebing et al. | |
| 5,603,713 A | 2/1997 | Aust et al. | |
| 5,609,593 A | 3/1997 | Errico et al. | |
| 5,615,965 A | 4/1997 | Saurat et al. | |
| 5,643,274 A | 7/1997 | Sander et al. | |
| 5,651,789 A | 7/1997 | Cotrel | |
| 5,672,176 A | 9/1997 | Biedermann et al. | |
| 5,676,640 A | 10/1997 | Biedermann | |
| 5,676,666 A | 10/1997 | Oxland et al. | |
| 5,702,395 A | 12/1997 | Hopf | |
| 5,702,452 A | 12/1997 | Argenson et al. | |
| 5,702,453 A | 12/1997 | Rabbe et al. | |
| 5,707,372 A | 1/1998 | Errico et al. | |
| 5,713,898 A | 2/1998 | Stucker et al. | |
| 5,716,355 A | 2/1998 | Jackson et al. | |
| 5,716,356 A | 2/1998 | Biedermann et al. | |
| 5,725,527 A | 3/1998 | Biedermann et al. | |
| 5,733,286 A * | 3/1998 | Errico et al. | 606/266 |
| 5,741,255 A | 4/1998 | Krag et al. | |
| 5,741,258 A | 4/1998 | Klaue et al. | |
| 5,743,907 A | 4/1998 | Asher et al. | |
| 5,743,911 A | 4/1998 | Cotrel | |
| 5,755,721 A | 5/1998 | Hearn | |
| 5,782,831 A | 7/1998 | Sherman et al. | |
| 5,798,264 A | 8/1998 | Pfreundschuh | |
| 5,810,816 A * | 9/1998 | Roussouly et al. | 606/246 |
| 5,810,823 A | 9/1998 | Klaue et al. | |
| 5,814,046 A | 9/1998 | Hopf | |
| 5,851,207 A | 12/1998 | Cesarone | |
| 5,873,878 A | 2/1999 | Harms et al. | |
| 5,879,352 A | 3/1999 | Filoso et al. | |
| 5,899,906 A | 5/1999 | Schenk | |
| 5,927,277 A * | 7/1999 | Baudino et al. | 600/386 |
| 5,928,233 A | 7/1999 | Apfelbaum et al. | |
| 5,961,517 A | 10/1999 | Biedermann et al. | |
| 5,976,135 A | 11/1999 | Sherman et al. | |
| 5,976,141 A | 11/1999 | Haag et al. | |
| 5,993,449 A | 11/1999 | Schlapfer et al. | |
| 6,027,533 A | 2/2000 | Olerud | |
| 6,059,790 A | 5/2000 | Sand et al. | |
| 6,063,090 A | 5/2000 | Schlapfer | |
| 6,086,590 A | 7/2000 | Margulies et al. | |
| 6,099,528 A | 8/2000 | Saurat | |
| 6,102,912 A | 8/2000 | Cazin et al. | |
| 6,106,526 A | 8/2000 | Harms et al. | |
| 6,120,503 A | 9/2000 | Michelson | |
| 6,139,459 A | 10/2000 | Suzuki | |
| 6,139,548 A | 10/2000 | Errico | |
| 6,139,549 A | 10/2000 | Keller | |
| D433,506 S | 11/2000 | Asfora | |
| 6,146,382 A | 11/2000 | Hurlbert | |
| 6,146,384 A | 11/2000 | Lee et al. | |
| 6,168,597 B1 | 1/2001 | Biedermann et al. | |
| 6,179,841 B1 | 1/2001 | Jackson | |
| 6,187,005 B1 | 2/2001 | Brace et al. | |
| 6,187,009 B1 | 2/2001 | Herzog et al. | |
| 6,235,034 B1 | 5/2001 | Bray | |
| 6,258,091 B1 | 7/2001 | Sevrain et al. | |
| 6,332,887 B1 | 12/2001 | Knox | |
| 6,342,056 B1 | 1/2002 | Mac-Thiong et al. | |
| 6,342,057 B1 | 1/2002 | Brace et al. | |
| 6,375,656 B1 | 4/2002 | Faure | |
| 6,387,097 B1 | 5/2002 | Alby | |
| 6,397,364 B1 | 5/2002 | Barkan | |
| 6,416,518 B1 | 7/2002 | DeMayo | |
| 6,419,678 B1 | 7/2002 | Asfora | |
| 6,524,315 B1 | 2/2003 | Selvitelli et al. | |
| 6,547,790 B2 | 4/2003 | Harkey, III et al. | |
| 6,565,571 B1 | 5/2003 | Jackowski et al. | |
| 6,616,671 B2 | 9/2003 | Landry et al. | |
| 6,635,062 B2 | 10/2003 | Ray, III et al. | |
| 6,669,733 B1 * | 12/2003 | Spierings | 623/23.48 |
| 6,712,818 B1 | 3/2004 | Michelson | |
| 6,755,829 B1 * | 6/2004 | Bono et al. | 606/308 |
| RE38,684 E | 1/2005 | Cesarone | |
| 6,860,884 B2 | 3/2005 | Shirado et al. | |
| 6,960,216 B2 | 11/2005 | Kolb et al. | |
| 7,094,242 B2 | 8/2006 | Ralph et al. | |
| 7,097,645 B2 | 8/2006 | Michelson | |
| 7,341,594 B2 | 3/2008 | Shluzas et al. | |
| 2001/0047172 A1 | 11/2001 | Foley et al. | |
| 2002/0049444 A1 | 4/2002 | Knox | |
| 2002/0082606 A1 | 6/2002 | Suddaby | |
| 2003/0100896 A1 | 5/2003 | Biedermann et al. | |
| 2003/0130659 A1* | 7/2003 | Haider | 606/61 |
| 2003/0187454 A1 | 10/2003 | Gill et al. | |
| 2003/0233098 A1 | 12/2003 | Markworth | |
| 2004/0015174 A1 | 1/2004 | Null et al. | |
| 2004/0019353 A1 | 1/2004 | Freid et al. | |
| 2004/0092947 A1 | 5/2004 | Foley | |
| 2004/0097950 A1 | 5/2004 | Foley et al. | |
| 2004/0176774 A1 | 9/2004 | Zubok et al. | |
| 2004/0181224 A1 | 9/2004 | Biedermann et al. | |
| 2004/0186473 A1 | 9/2004 | Cournoyer et al. | |
| 2005/0080417 A1 | 4/2005 | Alexis et al. | |
| 2005/0240185 A1 | 10/2005 | Boomer et al. | |

FOREIGN PATENT DOCUMENTS

| | | |
|---|---|---|
| WO | 03/007826 A1 | 1/2003 |
| WO | 03/024344 A1 | 3/2003 |
| WO | 2005/037115 A1 | 4/2005 |
| WO | 2005/051213 A1 | 6/2005 |

OTHER PUBLICATIONS

International Search Report for Application No. PCT/US06/25491, dated Sep. 10, 2007.

European Office Action for Application No. 06785918.1, dated Jun. 3, 2010.

Synthes Spine, "The Cervical Spine Locking Plate CSLP," (2000).

* cited by examiner

ORTHOPEDIC CLAMPING HOOK ASSEMBLY

FIELD OF THE INVENTION

The present invention relates to spinal fixation devices used in orthopedic surgery. More particularly, the present invention relates to an orthopedic hook assembly for coupling a spinal rod to a bone, such as the occipital bone.

BACKGROUND OF THE INVENTION

Spinal fixation systems may be used in orthopedic surgery to align, stabilize and/or fix a desired relationship between adjacent vertebral bodies and/or the occipital bone in the skull. Such systems typically include a spinal fixation element, such as a relatively rigid fixation rod or plate, that is coupled to a bone by attaching the element to various anchoring devices, such as hooks, bolts, wires or screws. The fixation element can extend between two bone regions to effect stabilization, positioning, reduction or fixation of the bones. The spinal fixation element can have a predetermined contour that has been designed according to the properties of the target implantation site and, once installed, the spinal fixation element holds the bones in a desired spatial relationship, either until desired healing or spinal fusion has occurred, or for some longer period of time.

Occipital hooks and hook techniques in the prior art rely on positioning bone screws drilled through the skull bone as a method of fixation. However, the bone screws inserted through the occipital bone can damage the fragile occipital bone and/or fail to provide adequate bone purchase. The failure to provide adequate bone purchase, which may be due to poor bone quality as a result of damage, osteoporosis or other conditions, may cause the screw to slip relative to the bone. In addition, prior art occipital hooks do not accommodate for variations in the thickness of the occipital bone.

SUMMARY OF THE INVENTION

The present invention provides an orthopedic clamping hook assembly for creating a rigid attachment into a bone, such as the occipital bone, of varying thicknesses and allowing attachment of a rod, such as a cervical rod, to the anchored orthopedic clamping hook assembly. The orthopedic clamping hook assembly allows for rigid fixation to the occiput or other location without use of bone anchoring screws, which may not be feasible in thin bone areas. The orthopedic clamping hook assembly includes a body forming a hook at one end for engaging bone and a rod-receiving portion at a second end for receiving a spinal fixation element, such as a rod, to be connected to the bone. The orthopedic clamping hook assembly further includes a compressor for fixing the hook to the bone and applying a compressive force to a bone disposed between the compressor and the hook to thereby retain the hook assembly in a selected position. The compressor may be axially movable relative to the body of the orthopedic clamping hook assembly to fix the hook assembly relative to the bone.

According to a first aspect of the invention, an orthopedic clamping hook assembly is provided, which comprises a body having a longitudinal axis, a rod-receiving portion disposed at a first end of the body, a hook for engaging a first side of a bone, which is disposed at a second end of the body, and a compressor coupled to the body for engaging a second side of the bone. The compressor applies a compressive force to the bone disposed between the hook and the compressor.

According to another aspect of the invention, a method of inserting an occipital clamping hook assembly in a body is provided. The method comprises the steps of inserting a hook through a hole in an occipital bone and into engagement with a first side of the occipital bone and moving a compressor coupled to the hook towards a second side of the occipital bone to apply a compressive force to the bone.

According to still another aspect of the invention, an occipital fixation system is provided, which comprises an occipital fixation plate including a body for stabilizing a spine of a patient and having at least one hole extending therethrough and an occipital clamping hook assembly. The occipital clamping hook assembly has a hook inserted through a first hole of the plate configured to engage a first side of an occipital bone. The occipital clamping hook assembly applies a compressive force to the plate and occipital bone.

BRIEF DESCRIPTION OF THE FIGURES

The foregoing and other objects, features and advantages of the invention will be apparent from the following description and apparent from the accompanying drawings, in which like reference characters refer to the same parts throughout the different views. The drawings illustrate principles of the invention and, although not to scale, show relative dimensions FIG. 1A a perspective view of an orthopedic clamping hook assembly, illustrated as an occipital clamping hook assembly, during installation in an occipital bone according to an illustrative embodiment of the invention.

FIG. 1B1 illustrates the orthopedic clamping hook assembly of FIG. 1A in an engaged position with the occipital bone according to an embodiment of the invention with a pin for locking the compressor in an engaged position with the bone.

FIG. 1B2 illustrates the orthopedic clamping hook assembly of FIG. 1A in an engaged position with the occipital bone according to an embodiment of the invention with a nut for locking the compressor in an engaged position with the bone.

DETAILED DESCRIPTION OF THE INVENTION

The present invention provides an improved orthopedic clamping hook assembly in a spinal fixation system. The invention will be described relative to use in the occipital region of a patient. One skilled in the art will recognize that the invention is not limited to use in the occipital bone, other bones, or in spinal surgery, and that the instrument and methods described herein can be adapted for use with any suitable surgical device to be moved into a selected position in a variety of medical procedures. The present invention will be described below relative to certain exemplary embodiments to provide an overall understanding of the principles of the structure, function, manufacture, and use of the instruments disclosed herein. Those skilled in the art will appreciate that the present invention may be implemented in a number of different applications and embodiments and is not specifically limited in its application to the particular embodiments depicted herein.

Figure 1A:
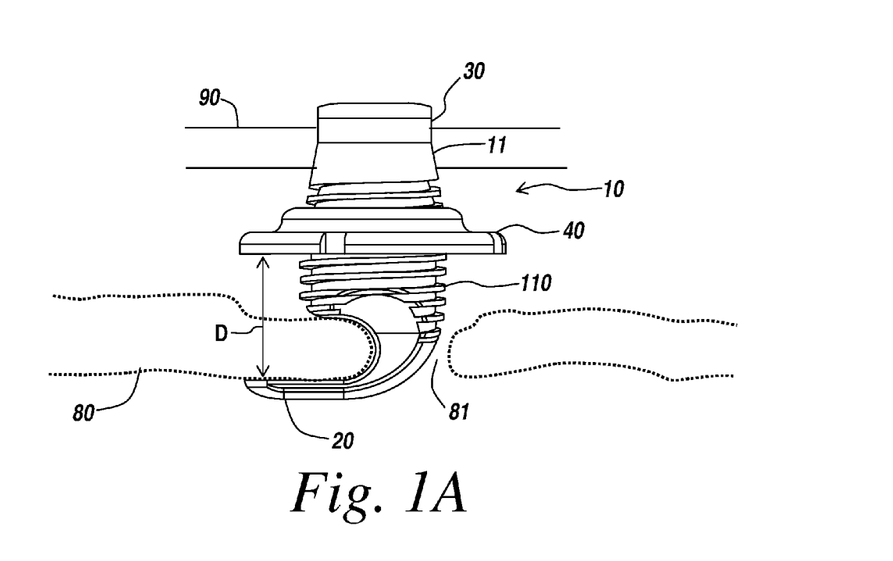

FIGS. 1A-7 illustrate an orthopedic clamping hook assembly, illustrated as an occipital clamping hook assembly 10, according to a first illustrative embodiment of the invention. The occipital clamping hook assembly 10 may be used to create a rigid attachment into an occipital bone 80 of varying thickness and/or different occipital bones of different thicknesses subsequent fixation of a spinal rod 90 to the occipital bone 80, as shown in FIGS. 1A and 1B. One skilled in the art will recognize that the assembly 10 may be used to couple any fixation device to any type of bone, in any location within the body, and is not limited to use with the occipital bone. The illustrative occipital clamping hook assembly 10 applies a compressive force to secure the assembly to the bone 80, without requiring use of bone screws.

The occipital clamping hook assembly 10 shown in FIGS. 1A-7 includes a body 11 forming a hook 20 at a first end for engaging bone and a rod-receiving portion 30 at a second end for receiving a rod or other spinal fixation element to be fixed to the bone. As shown in FIGS. 1A and 1B, the hook portion 20 of the assembly 10 is inserted through a hole 81 in the occipital bone 80, or at the edge of a deformity, and engages the bone on an inside surface. The hole 81 may be formed by an instrument, such as a drill or burr, or may comprise an edge of a deformity formed in the skull. Alternatively, the hole 81 may be formed as a result of tumor removal, after which the occipital clamping hook assembly 10 is implanted. In the illustrative embodiment, the hook 20 and the rod-receiving portion 30 are integrally formed with the body 11, though one skilled in the art will recognize that the hook 20 and rod-receiving portion may be coupled to the body through any suitable means known in the art.

Figure 1B:
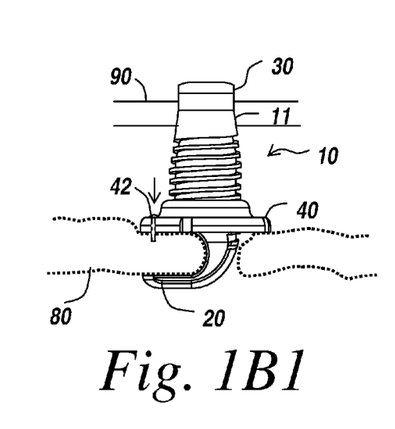
Figure 1B:
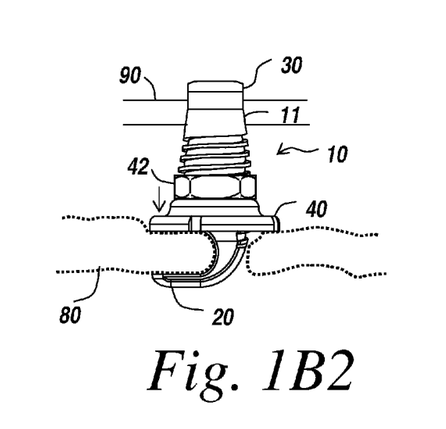
Figures 2, 3, 4:
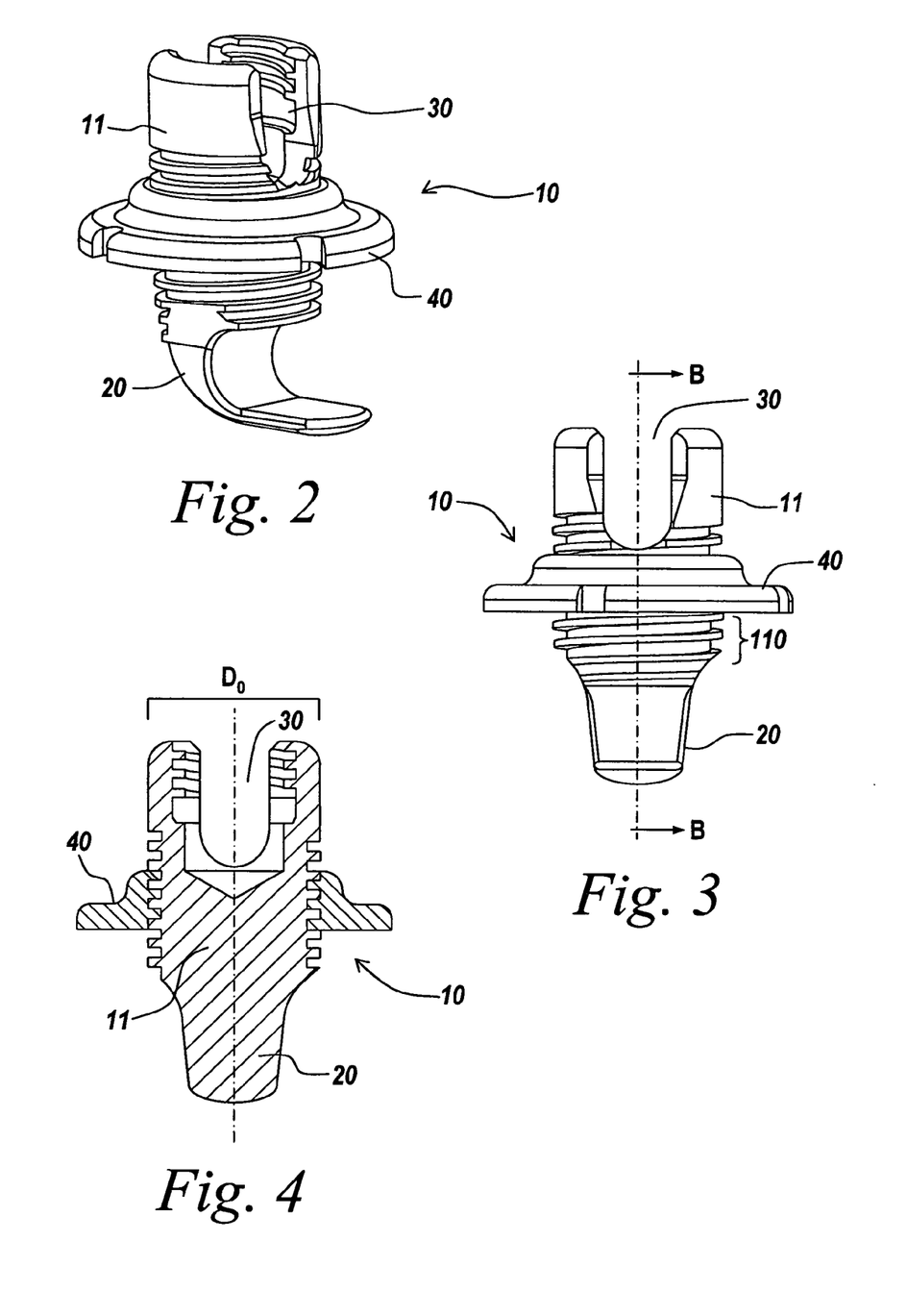
FIG. 2 is a perspective view of the orthopedic clamping hook assembly of FIG. 1.
FIG. 3 is front view of the orthopedic clamping hook assembly of FIG. 1.
FIG. 4 is a cross-sectional side view of the orthopedic clamping hook assembly through section B-B of FIG. 3.
Figure 5:
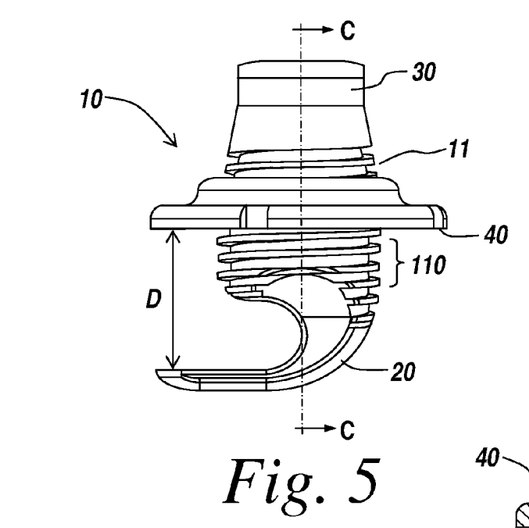
FIG. 5 is a side view of the orthopedic clamping hook assembly of FIG. 1.
Figure 6:
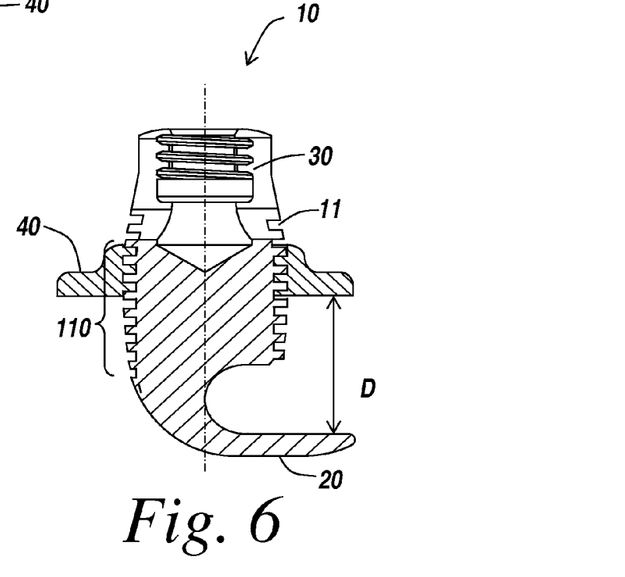
FIG. 6 is a cross-sectional view of the orthopedic clamping hook assembly through section C-C of FIG. 5.
Figure 7:
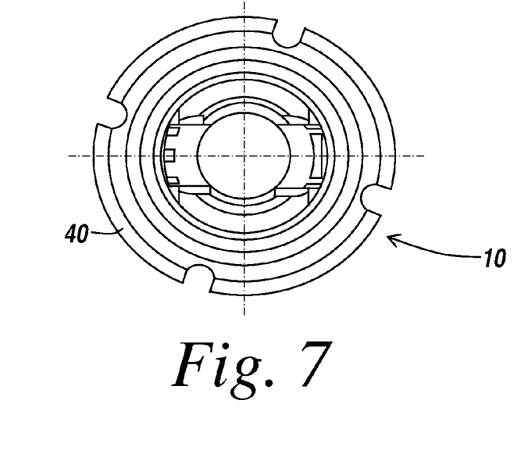
FIG. 7 is a top view of the orthopedic clamping hook assembly of FIG. 1.

The occipital clamping hook assembly 10 further includes a compressor 40 coupled to the body 11 for applying a compressive force to the occipital bone 80 and securing the assembly 10 relative to the bone 80. The compressor 40 is separated from the hook 20 by a variable separation distance D to form a region for holding the bone 80 therebetween. The compressor is axially movable relative to the body 11 to sandwich and compress the bone 80 between the compressor 40 and the hook 20, as shown in FIG. 1B. The variable separation distance D between the hook 20 and the compressor 40 allows for accommodation of bones having varying thicknesses and strengths, as well as variation in the amount of compressive force applied by the compressor 40 to secure the assembly 10 to the bone 80.

Prior to insertion, the compressor 40 is preferably positioned so as to be separated from the hook 20 to facilitate insertion of the hook into the bone, as shown in FIG. 1A. Then, after the hook is inserted into the bone, the compressor 40 may be moved into an engaged position to secure the assembly 10 relative to the bone 80, as shown in FIG. 1B. In the illustrative embodiment, the compressor 40 moves over threads 110 towards the bone 80 and hook 20 to sandwich and compress the bone 80 between the compressor 40 and the hook 20, though one skilled in the art will recognize that any suitable means for securing the occipital clamping hook assembly 10 to the bone 80 may be used in accordance with the teachings of the invention.

Figure 8A:
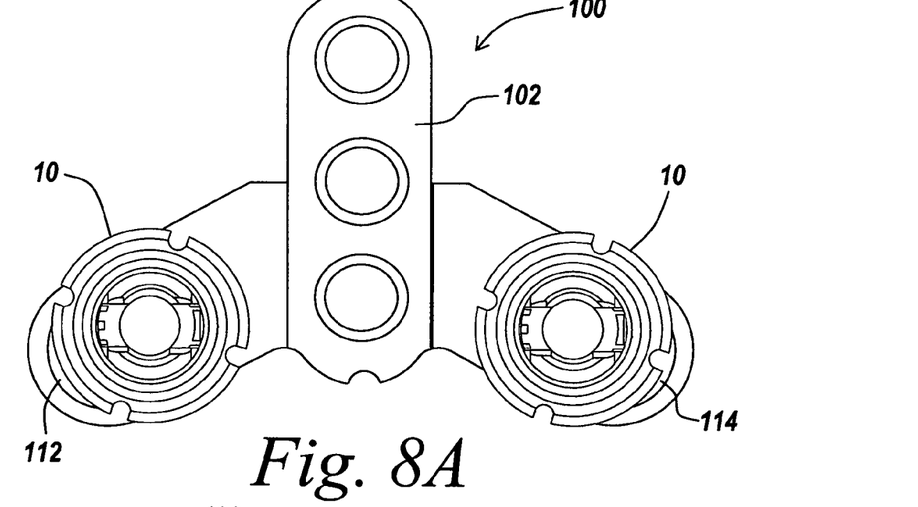
FIGS. 8A-8C illustrate an occipital fixation system implementing a plurality of orthopedic clamping hook assemblies according to an embodiment of the invention.
Figure 8B:
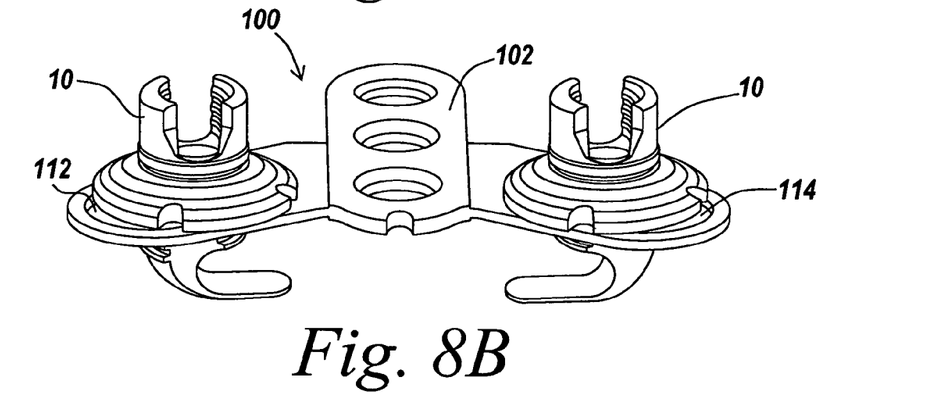
Figure 8C:
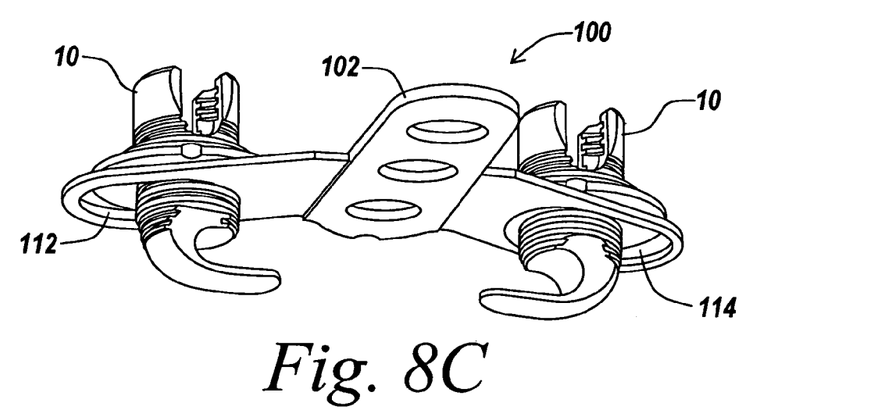

As shown in FIGS. 8A-8C, the illustrative occipital clamping hook assembly 10 may be implemented in a spinal fixation system 100 including an occipital fixation plate 102 to fix the occipital fixation plate 102 relative to the occipital bone, as well as to connect spinal rods to the plate 102 and occipital bone. The occipital fixation plate 102 comprises a substantially flat body for stabilizing the spine including openings 112, 114 for receiving the occipital clamping assemblies 10 for securing the plate 102 to the occipital bone. The openings 112, 114 align with openings, such as the opening 81 in FIGS. 1A and 1B, in the occipital bone 80. The hook 20 of the assembly 10 is inserted through the aligned openings in the plate and occipital bone, and engages the occipital bone on an inner surface of the bone opposite the plate 102, such that the body 11 and rod-receiving portion 30 extends through the corresponding opening 112 or 114 of the plate 102. The compressor 40 of the clamping hook assembly 10 then advances towards the hook 20 to compress the plate 102 and occipital bone between the compressor 40 and the hook 20, thereby securing the hook assembly 10 and the occipital fixation plate 102 to the occipital bone.

Figure 9A:
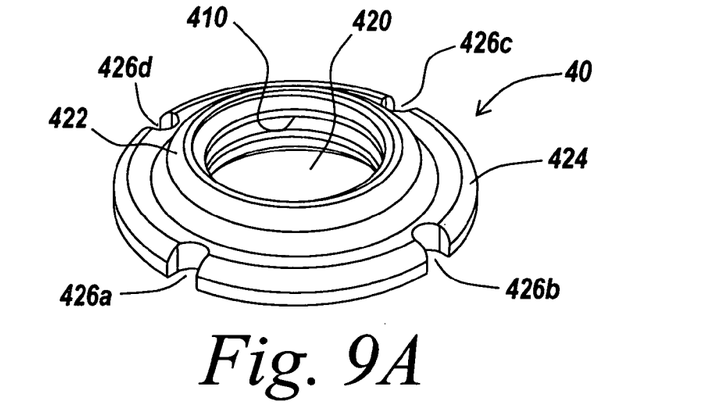
FIGS. 9A-9C illustrate an embodiment of the compressor component of the illustrative orthopedic clamping hook assembly of FIGS. 1-8C.
Figure 9B:
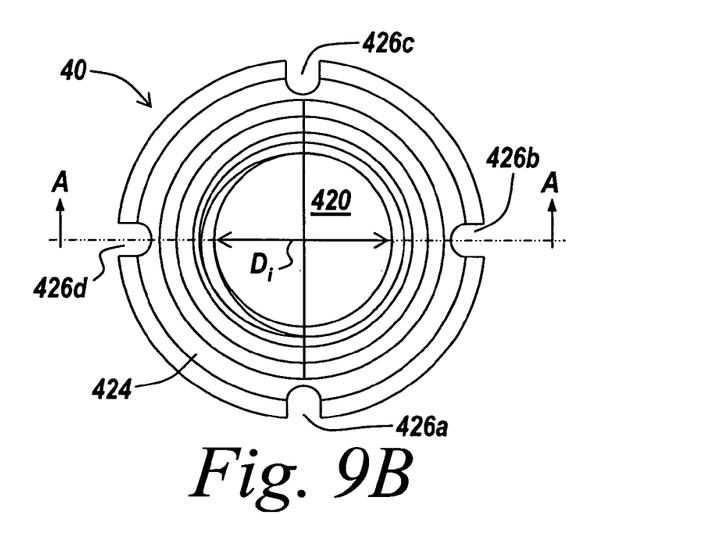
Figure 9C:
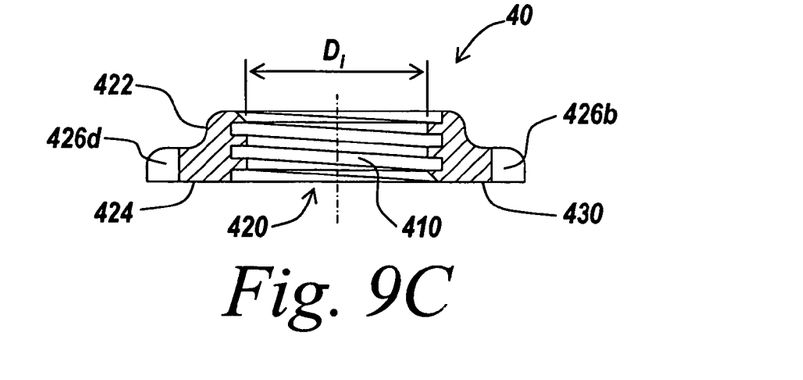

The compressor 40 in the occipital clamping hook assembly 10 of the invention may have any suitable size, shape and configuration suitable for applying a compressive force to an object sandwiched between the compressor 40 and a corresponding hook 20. FIGS. 9A-9C illustrate in detail an embodiment of the compressor 40 of the illustrative hook assembly 10 shown FIGS. 1-8C. In the embodiment shown in FIGS. 1-9C, the compressor 40 comprises a substantially disc-shaped flange having a central opening 420 configured to receive and encircle the body 11. The body 11 of the illustrative hook assembly 10, illustrated in FIGS. 10A-10F, preferably has a substantially cylindrical shape matching the central opening 420, which has an inner diameter $D_i$ that is slightly larger than the outer diameter $D_o$ of the body 11 to accommodate the body 11 in the central opening 420. The compressor 40 includes a bottom surface 430 for contacting bone 80 or a plate 102, and applying a compressive force to the bone sandwiched between the compressor 40 and the hook 20.

The compressor 40 may be movably coupled to the body 11 through any suitable means known in the art. For example, mating threads may be used to facilitate relative, controlled movement of the compressor 40 relative to the body 11. In the embodiment of FIGS. 1-9C, the body 11 includes a set of threads 110 formed on an outer surface thereof. The illustrative compressor 40 includes a set of threads 410 formed on an inner surface of the central opening 420 configured to mate with the set of threads 110 on the body 11. The threads in the sets 110 and 410 extend substantially perpendicular to the longitudinal axis A-A of the body 11, so that rotation of the compressor 40 about the longitudinal axis A-A translates into axial movement of the compressor 40 relative to the body 11 and the hook 20.

The compressor 40 preferably has a ridge 422 surrounding the central opening 420 and a thinner projection 424 extending from and around the central opening 420. The ridge 422 increases the axial thickness of the compressor around the central opening 420 to accommodate more threads, facilitating the movable connection of the compressor 40 to the body 11. According to one embodiment, the compressor 40 further includes peripheral openings 426a-426d about the perimeter of the projection 424 for receiving a tool for rotating the compressor 40 about the longitudinal axis A-A of the body 11 to move the compressor 40 into engagement with the bone.

The bottom surface 430 of the flanged compressor 40 may be configured to engage or otherwise interface with bone 80 or a fixation plate 102. For example, the bottom surface 430 may be contoured or shaped to match one or more bone features. The bottom surface 430 may include teeth or other textured surface for engaging the occipital bone or a spinal fixation plate. Alternatively, or in addition to engagement means, the bottom surface may be cushioned or include another element for absorbing forces on the compressor 40.

A washer (not shown) may also be used between the compressor 40 and the hook 20 to take up tolerance during clamping of the assembly 10 to the occipital bone, or another bone engaged by the assembly, using the compressor 40.

The compressor 40 may also have a lock 42 for locking the compressor 40 in an engaged position with the bone. The lock 42 may be deployed manually when the compressor 40 clamps the bone, or automatically when a predetermined threshold force is reached. The lock 42 may comprise any suitable device known in the art for locking the compressor in a selected position relative to the body 11. For example, the lock 42 may be formed by forming a hole in the compressor configured to receive a pin, which may be inserted through the hole and into the engaged bone to prevent further rotation of the compressor 40, as illustrated in FIG. 1B1. Another embodiment of the lock 42 may comprise a nut tightened on top of the compressor 40 after the compressor reaches a suitable position to prevent further rotation of the compressor, or any other suitable means for preventing derotation of the compressor after engagement, as illustrated in FIG. 1B2.

One skilled in the art will recognize that the compressor 40 may have any suitable size, shaped and configuration for clamping the occipital clamping hook assembly 10 to an occipital bone, and is not limited to the embodiment shown in FIGS. 1-9C.

FIGS. 10A-10F illustrate the body 11 of the illustrative occipital clamping hook assembly 10 of FIGS. 1-8C. In the illustrative embodiment, the rod-receiving portion 30 of the body includes a substantially U-shaped slot 32 for receiving a spinal rod or other spinal fixation element. The slot 32 extends along an axis B-B and includes internal threads 320 for receiving a capping element or other suitable device for locking a rod in the slot 32. One skilled in the art will recognize that the rod-receiving portion 30 may have any suitable configuration for receiving a rod or other spinal fixation element to be coupled to the occipital bone using the occipital clamping hook assembly of the present invention.

The hook 20 of the illustrative occipital clamping hook assembly of FIGS. 1-10F extends from the first, bottom end of the body 11 and may have any suitable size, shape and configuration for engaging bone, in particular the occipital bone. The illustrative hook 20 comprises a tapering protrusion that has a curved connecting portion 21 where the rod extends from the body 11 and a straight end portion 22 where the hook 20 engages the bone. The width W of the end portion 22 may remain substantially constant or may be tapered. The end portion 22 preferably includes a flat inner surface 24 that lies flat against the bone when the hook assembly is in an engaged position, as shown in FIG. 1B. Alternatively, the inner surface 24 may be contoured or textured to facilitate engagement with the bone. The tip 22a of the end portion 22 may be curved, as shown in FIGS. 10a-10f, or may have another suitable configuration. The end portion 22 may extend from the curved connecting portion 21 (aligned with the axis A-A) by any selected amount suitable for engaging bone. In the embodiment of FIGS. 1-10f, the end portion 22 has a length such that the tip 22a aligns with the edge of the compressor flange when the assembly 10 is assembled, as shown in FIGS. 1A-7. However, one skilled in the art will recognize that the hooking end portion 22 may have any suitable size, shape, length and configuration.

Figure 10A:
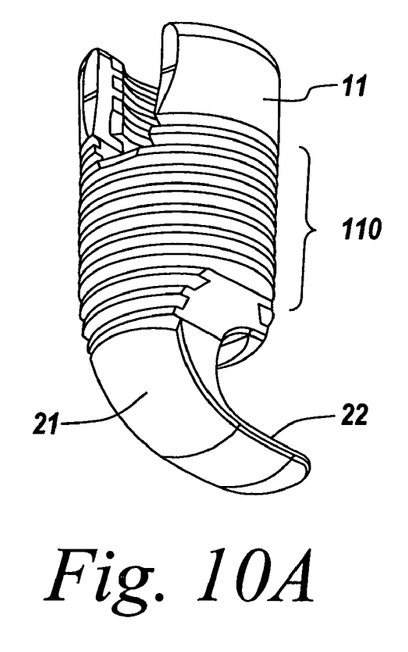
FIGS. 10A-10F illustrate the body component of the illustrative orthopedic clamping hook assembly of FIGS. 1-8C.
Figure 10B:
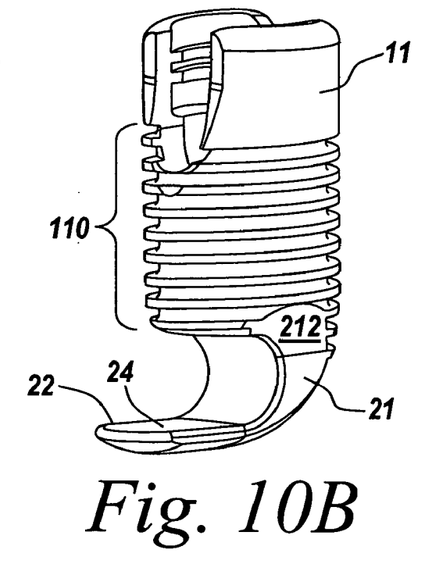
Figure 10C:
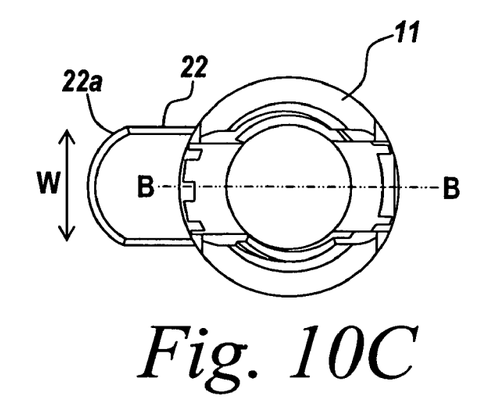
Figure 10D:
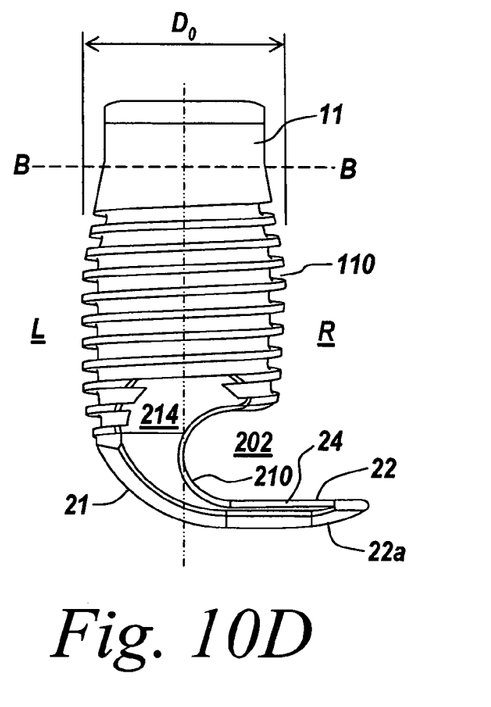
Figure 10E:
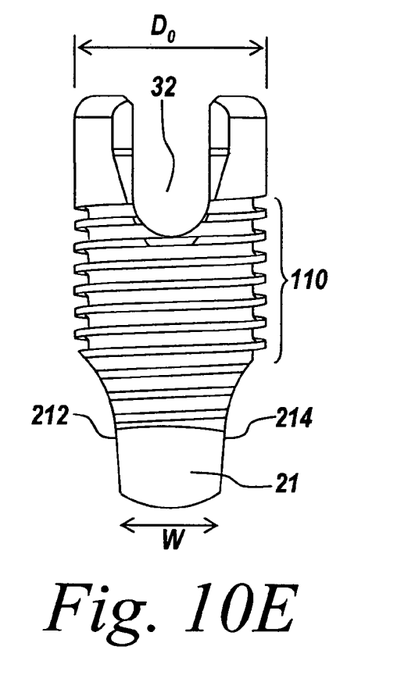
Figure 10F:
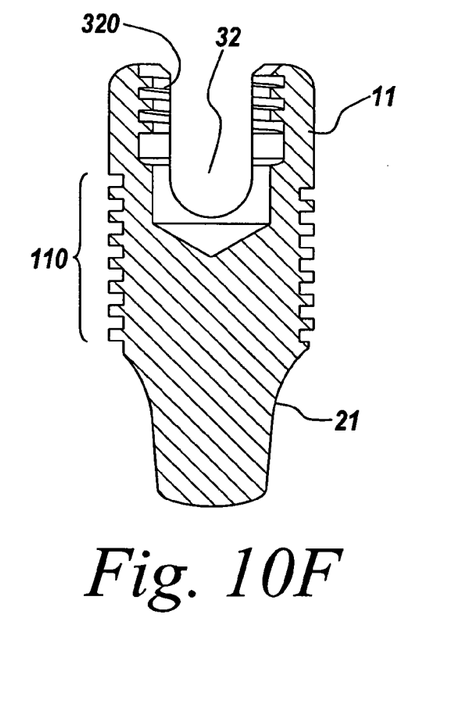
Figure 11A:
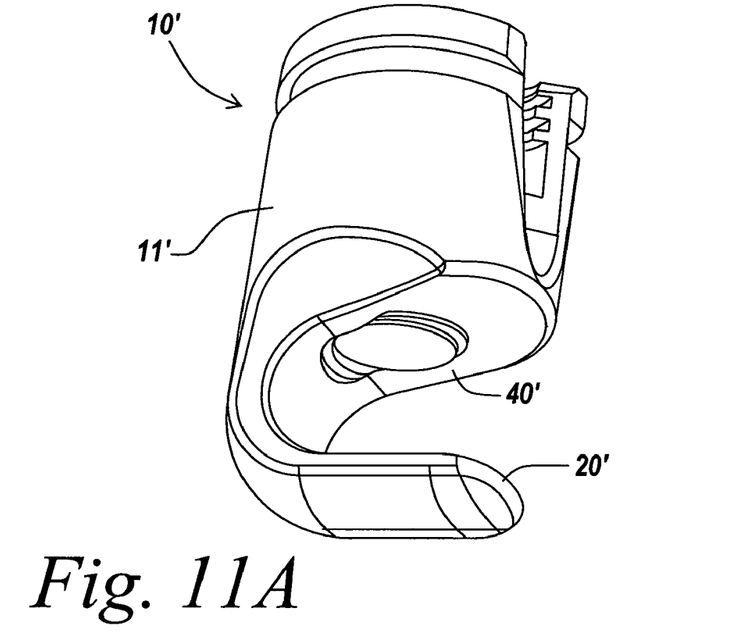
FIGS. 11A-11D illustrate an orthopedic clamping hook assembly according to another embodiment of the invention.
Figure 11B:
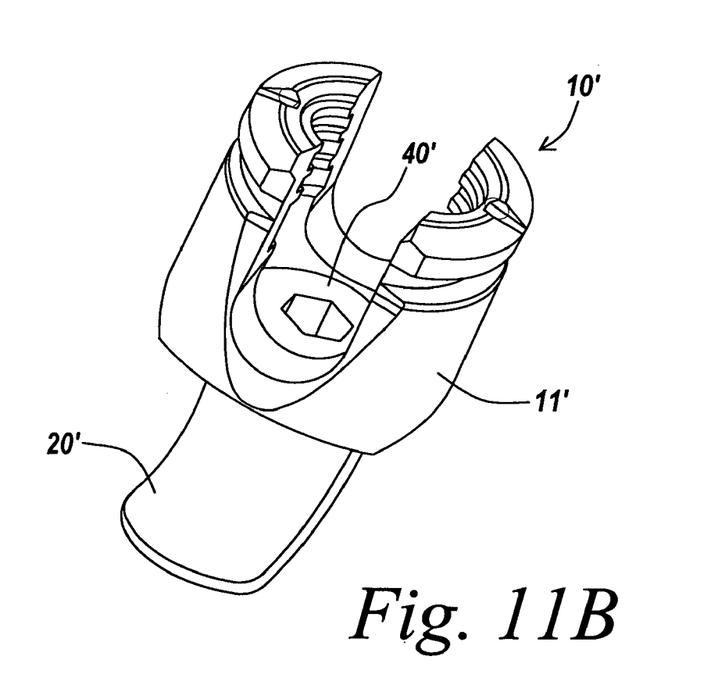
Figure 11C:
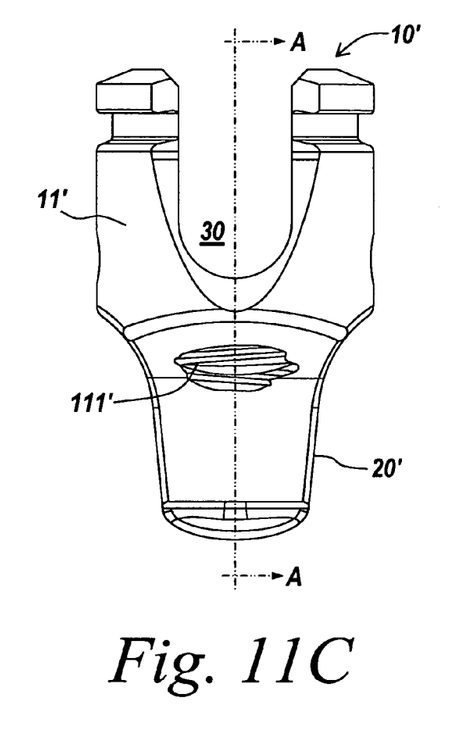
Figure 11D:
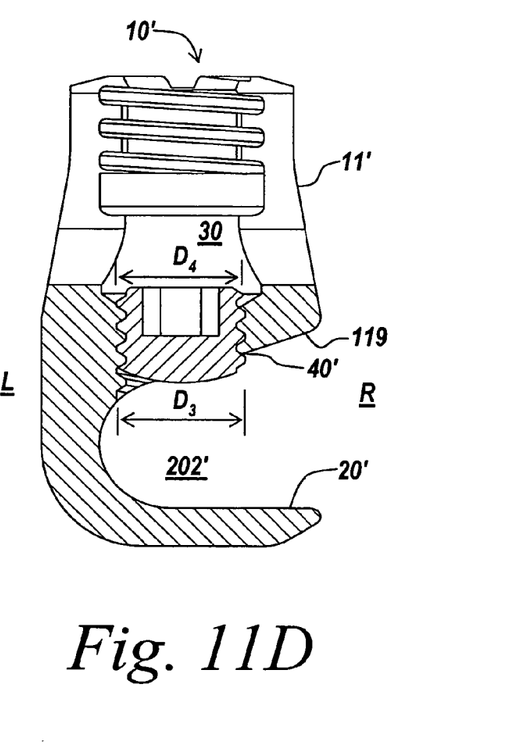
Figures 12A, 12D:
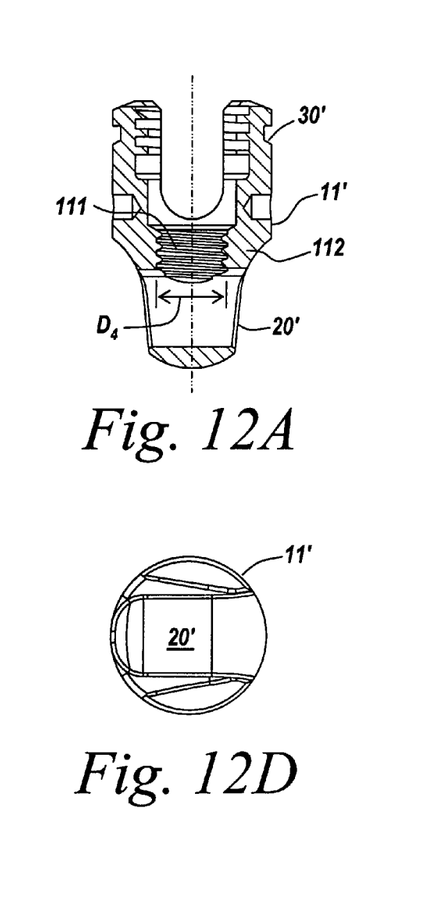
FIGS. 12A-12F illustrate the body of the orthopedic clamping hook assembly of FIGS. 11A-11D.
Figure 12B:
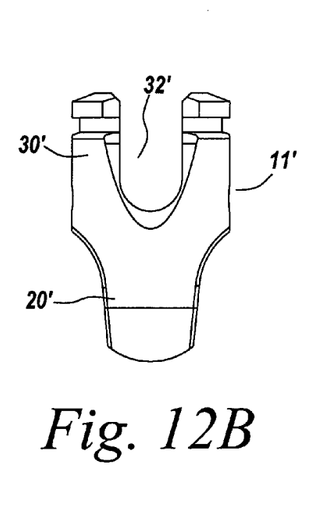
Figure 12C:
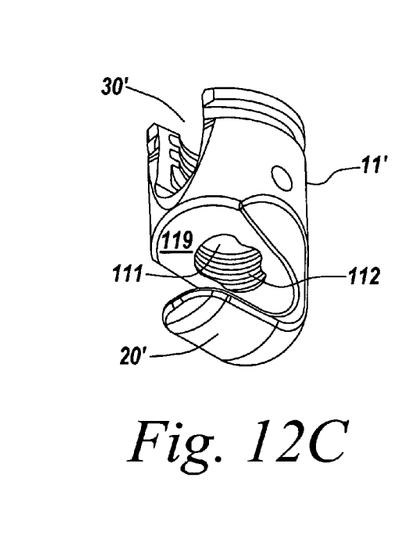
Figure 12E:
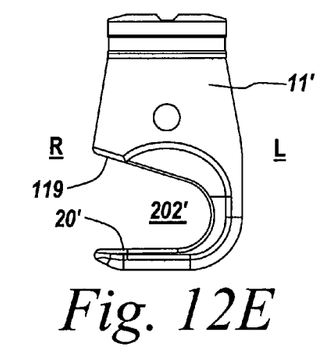
Figure 12F:
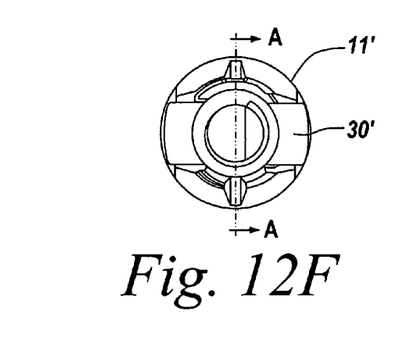

In the illustrative embodiment, the curved connecting portion 21 of the hook 20 extends from a first side L of the body 11 (i.e., a half extending of a first side of a plane extending through the longitudinal axis) and creates a space 202 between a second side R of the body on an opposite side of the plane extending through the longitudinal axis and the end 22 of the hook 20, as shown in FIG. 10D. The curved connecting portion 21 has a curved inner wall 210 that curves about 180 degrees and intersects the inner wall 24 of the end portion. The side walls 212, 214 of the connecting portion 21 may be substantially flat and the outer surface 216 may also be curved. One skilled in the art will recognize that the hook 20 may have any suitable configuration suitable for engaging an occipital bone.

According to one embodiment, the hook 20 may be selectively movable relative to the body 11 and then locked in a particular configuration relative to the body and/or the bone.

While the illustrative occipital clamping hook assembly 10 of FIGS. 1-10F includes a single hook 20, the assembly may alternatively include multiple hooks disposed at the first end of the body 11 and configured to engage bone.

The external threads 110 for coupling the compressor 40 to the body 11 preferably extend from upper portion of the body around bottom of the slot 32 to the connecting portion 21 of the hook 20. However, the threads, or other suitable engagement means, may alternatively have any suitable size, length, location and configuration.

FIGS. 11A-11D illustrate another embodiment of an orthopedic clamping hook assembly, illustrated as an occipital clamping hook assembly 10', according to the present invention. Components of the occipital clamping hook assembly 10' corresponding to the components of the occipital clamping hook assembly 10 of FIGS. 1-10F are represented by the same number, differentiated by a prime. The occipital clamping hook assembly 10' of FIGS. 11A-11D includes an internal compressor 40' for applying a compressive force to retain a bone between the hook 20' and compressor 40'. Referring to FIGS. 12A-12F, the body 11' of the occipital clamping hook assembly 10' includes an axially extending internal passageway 111 below the rod-receiving portion 30 for receiving the compressor 40'. The compressor 40', shown in FIG. 13 comprises a substantially cylindrical-shaped solid object having an outer diameter $D_3$ that is slightly less than an inner diameter $D_4$ of the axially extending internal passageway 111. The axially extending internal passageway 111 includes a set of internal threads 112 located on an interior surface thereof. The compressor 40' includes a set of external threads 402 on an outer surface thereof configured to mate with the internal threads 112, such that rotation of the compressor 40' about the axis A-A advances or retracts the compressor 40' along the passageway. The bottom of the axially extending internal passageway 111 opens to a region 202' between the hook 20' and the compressor 40', which protrudes from the opening by a selected distance to apply a force to a bone inserted in the region 202'.

Figure 13:
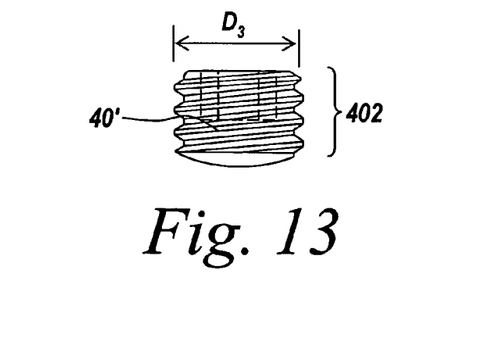
FIG. 13 illustrates the compressor in the orthopedic clamping hook assembly of FIGS. 11A-11C.

The compressor 40' includes a substantially hexagonal opening on the top surface thereof for receiving a driver for rotating the compressor.

In the embodiment shown in FIGS. 11A-11D, the hook 20' extends from a first side wall on a first side L of the body 11' to an end portion that aligns with an opposite wall on an opposite side R the body and forms the space 202' between the body 11' and the hook for receiving bone. However, one skilled in the art will recognize that the hook 20' can have any suitable length suitable for engaging bone. In the illustrative embodiment, the body 11' has a slanted bottom surface 119 through which protrudes the compressor 40'. The slanted surface 119 facilitates insertion of the hook 20' below the bone prior to engagement by the compressor 40'.

According to another embodiment of the invention, the rod-receiving portion of an orthopedic clamping hook assembly, such as an occipital clamping hook assembly, and/or a hook portion of an orthopedic clamping hook assembly, such as an occipital clamping hook assembly, may be movable relative to the body of the assembly. For example, FIGS. 14A-14F illustrate an embodiment of an occipital clamping hook assembly 10" including a rod-receiving portion 30" that is movable relative to a body portion 11" to allow for angulation of one portion of the assembly relative to another portion of the assembly and bone coupled to the assembly. The assembly 10" may allow for the rod-receiving portion 30" to pivot in all directions about a 360° arc relative to the body 11" or in one or more selective directions. The use of a movable rod-receiving portion facilitates insertion and connection of a spinal rod that extends at in a non-parallel direction relative to the bone and/or the opening in the bone.

The body 11" of the movable occipital clamping hook assembly 10" includes a drive shaft 113 and a cylindrical base portion 115 having a central opening 116 for receiving the drive shaft 113. The drive shaft 113 includes a joint portion 117 for movably mounting the rod-receiving portion 30" through means known in the art. An example of means for movably mounting a rod-receiving portion or other suitable head portion to a shaft is described in detail in Application Publication Number US 2004/0186473 entitled "Spinal Fixation Devices of Improved Strength and Rigidity", U.S. Patent Application Publication Number US 2004/0181224 entitled "Anchoring Element for Use in Spine or Bone Surgery, Methods for Use and Production Thereof" and U.S. Patent Application Publication Number US 2003/0100896, entitled "Element With a Shank and a Holding Element Connected to It for Connecting to a Rod", the contents of which are herein incorporated by reference.

The base portion 115 includes threads 110" formed on an outer surface thereof for mating with threads 410 on a corresponding compressor 40" to allow the compressor 40" to move relative to the hook portion 20" to secure and compress a bone therebetween.

Figures 14A, 14B:
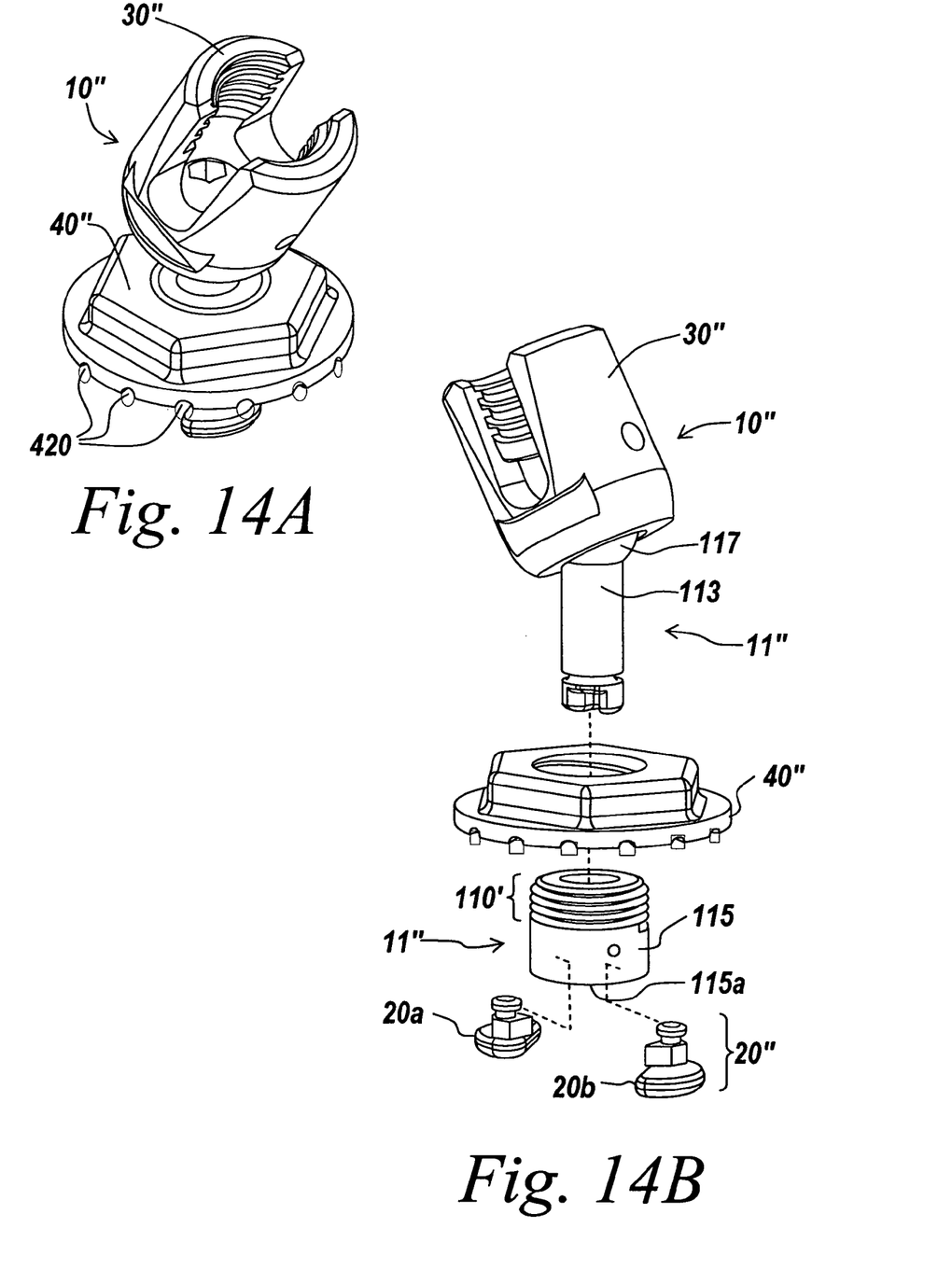
FIGS. 14A-14F illustrate an orthopedic clamping hook assembly including a relatively movable rod-receiving portion and a relatively movable hook portion according to another embodiment of the invention.
Figure 14C:
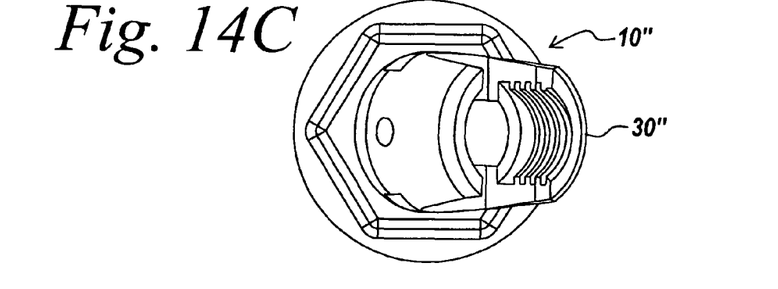
Figure 14D:
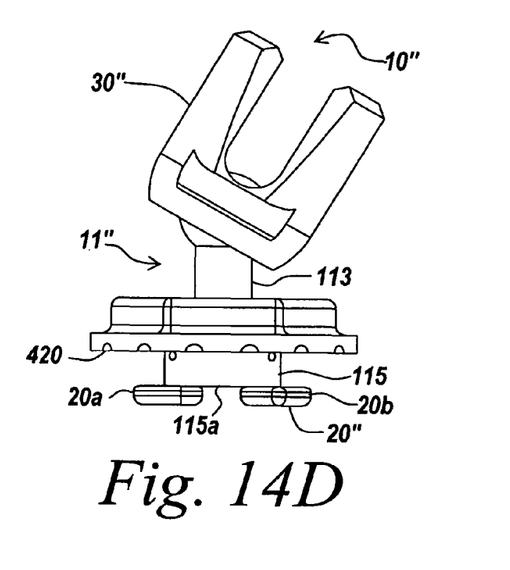
Figure 14E:
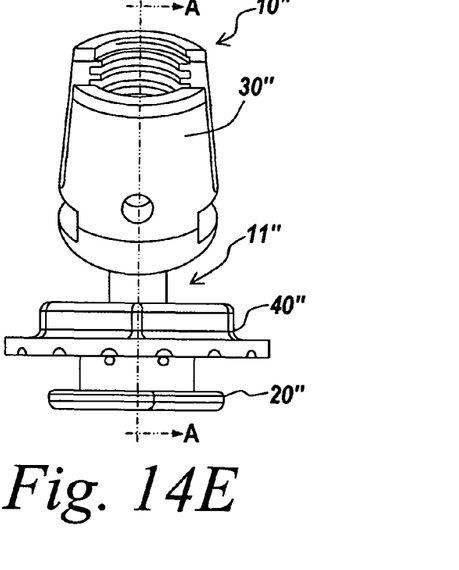
Figure 14F:
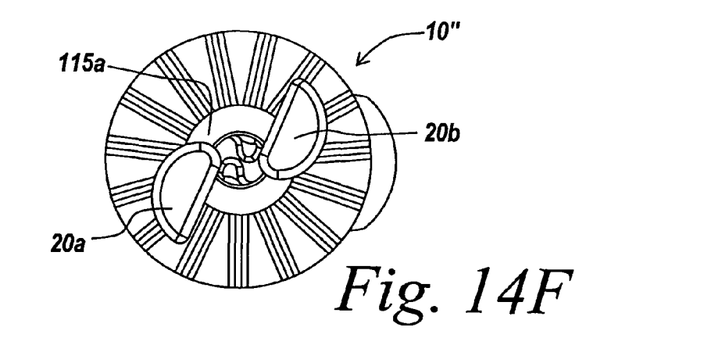

In the occipital clamping hook assembly 10" shown in FIGS. 14A-14F, the hook portion 20" is also movable relative to the body 11". The illustrative hook portion 20" comprises two protrusions 20a, 20b movably coupled to a bottom surface 115a of the base portion 115, though one skilled in the art will recognize that a movable hook portion may comprise one or several hooks. In an unengaged position, shown in FIG. 14E, the protrusions 20a, 20b are pulled in under the bottom surface 115a. In an engaged position, as shown in FIGS. 14A, 14D and 14F, the protrusions 20a, 20b shift position and extend from the bottom surface 115a to form hooks for engaging the bone. According to one embodiment, a rotation of the drive shaft about the axis A-A serves to move the protrusions 20a, 20b from an unengaged position to an engaged position, though one skilled in the art will recognize that any suitable means for operating the movable hooks may be used.

The occipital clamping hook assembly 10" shown in FIGS. 14A-14F further includes grooves 420 formed on a bottom surface of the compressor 40" forming teeth for engaging bone, as described above.

An orthopedic clamping hook assembly according to the illustrative embodiments of the invention provides significant advantages over prior systems and methods for coupling a fixation device to a bone, such as an occipital bone. For example, prior systems generally require use of bone screws, which can damage fragile bone. The orthopedic clamping hook assembly of the illustrative embodiments may utilize a variable compressive force to fix the assembly and associated spinal fixation device to a bone. The orthopedic clamping hook assembly of the illustrative embodiments may be flexible to accommodate bones of varying thickness. In addition, an orthopedic clamping hook assembly of an embodiment of the invention may enable relative movement of components to accommodate other fixation devices and/or contours in the bone structure.

The present invention has been described relative to an illustrative embodiment and application in the occipital bone. Since certain changes may be made in the above constructions without departing from the scope of the invention, it is intended that all matter contained in the above description or shown in the accompanying drawings be interpreted as illustrative and not in a limiting sense. For example, one skilled in the art will recognize that the assembly of the illustrative embodiment of the invention is not limited to use with spinal rods and can be used with any suitable implant for any suitable orthopedic system. In addition, the assembly is not limited to use in the occipital region of a patient and may be used in any suitable location of a patient where it is desirable to anchor an implant to a particular location of the patient's body.

It is also to be understood that the following claims are to cover all generic and specific features of the invention described herein, and all statements of the scope of the invention which, as a matter of language, might be said to fall therebetween.

The invention claimed is:

1. An orthopedic clamping hook assembly comprising:
 a body having a longitudinal axis;
 a rod-receiving portion disposed at a first end of the body;
 a hook disposed at a second end of the body for engaging a first side of a bone, the hook comprising a curved portion extending from the body, and a straight end portion extending from the curved portion and for engaging the first side of the bone, the straight end portion being disposed substantially perpendicular to the rod-receiving portion and extending beyond a width of the body; and
 a compressor encircling the body below the rod receiving portion for engaging a second side of the bone, the straight end portion of the hook having a length such that a tip of the straight end portion aligns with an outer edge of the compressor to apply a compressive force to the bone when the bone is disposed between the hook and the compressor, wherein when the compressor is in an engaged position where the compressor engages the bone, a compressive force is maintained on the bone disposed between the compressor and the hook, wherein the body comprises a first set of threads for mating with a second set of threads formed on the compressor to movably couple the body and the compressor, the first set of threads extending from a portion of the body around the rod-receiving portion to the curved portion of the hook.

2. The orthopedic clamping hook assembly of claim 1, wherein the compressor is axially movable relative to the body.

3. The orthopedic clamping hook assembly of claim 1, wherein the compressor and hook are separated by a variable separation distance.

4. The orthopedic clamping hook assembly of claim 1, wherein the first set of threads is located on an outer surface of the body.

5. The orthopedic clamping hook assembly of claim 1, wherein the body includes an axially extending inner passageway, and a third set of threads is located on an interior surface of the axially extending inner passageway of the body.

6. The orthopedic clamping hook assembly of claim 1, wherein the compressor comprises a flange encircling the body.

7. The orthopedic clamping hook assembly of claim 1, wherein the compressor is substantially cylindrical-shaped and axially movable along an axially extending passageway formed in the body.

8. The orthopedic clamping hook assembly of claim 1, further comprising a locking mechanism for locking the compressor in an engaged position when the compressor engages and compresses the bone.

9. An occipital clamping hook assembly, comprising:
a body having a longitudinal axis;
a rod-receiving portion disposed at a first end of the body;
a hook disposed at a second end of the body and configured to engage a side of an occipital bone, the hook comprising a curved portion extending from the body, and a straight end portion extending from the curved portion and for engaging the side of the occipital bone; and
a compressor encircling the body below the rod receiving portion, an outer edge of the compressor aligning with an end tip of the hook so that a compressive force is applied to the occipital bone when the bone is disposed between the hook and the compressor, the compressor having a central opening, wherein when the compressor is in an engaged position where the compressor engages the bone, a compressive force is maintained on the bone disposed between the compressor and the hook, wherein the body comprises a first set of threads on an outer surface of the body, the first set of threads extending from a portion of the body around the rod-receiving portion to the curved portion of the hook, wherein the compressor comprises a second set of threads on an inner surface of the compressor so that the compressor axially moves over the threads of the body.

10. The occipital clamping hook assembly of claim 9, wherein the hook, and the rod-receiving portion are integrally formed with the body.

11. The occipital clamping hook assembly of claim 9, wherein the compressor comprises a substantially disc-shaped flange having a central opening configured to receive and encircle the body.

12. The occipital clamping hook assembly of claim 9, wherein the body has a substantially cylindrical shape.

13. The occipital clamping hook assembly of claim 9, wherein an inner diameter of the compressor is larger than an outer diameter of the body to accommodate the body in the central opening.

14. A clamping hook assembly, comprising:
a body having a longitudinal axis extending in an axial direction;
a rod-receiving portion disposed at a first end of the body;
a hook disposed at a second end of the body, the hook comprising a curved portion extending from the body, and a straight end portion extending from the curved portion; and
a compressor encircling the body below the rod receiving portion, the compressor comprising:
a central opening configured to fit around the body of the clamping hook assembly;
a closed ridge surrounding the central opening, wherein the closed ridge increases the thickness of the compressor around the central opening;
a projection extending from and provided around the central opening, the projection being thinner than the closed ridge in the axial direction and wider than the closed ridge in a radial direction of the body; and
a plurality of peripheral openings provided on a perimeter of the projection for receiving a tool to rotate the compressor about a longitudinal axis of the body of the clamping hook assembly, wherein the compressor is free of a protrusion extending beyond a bottom surface of the projection opposite the closed ridge,
wherein the body comprises a first set of threads for mating with a second set of threads formed on the compressor to movably couple the body and the compressor, the first set of threads extending from a portion of the body around the rod-receiving portion to the curved portion of the hook.

* * * * *